United States Patent [19]

Kamei et al.

[11] Patent Number: 4,598,998
[45] Date of Patent: Jul. 8, 1986

[54] SCREW SURFACE FLAW INSPECTION METHOD AND AN APPARATUS THEREFOR

[75] Inventors: Mitsuhito Kamei, Hyogo; Shin Nemoto, Osaka; Souji Ishimoto, Yamatokohriyama, all of Japan

[73] Assignees: Sumitomo Kinzoku Kogyo Kabushiki Kaisha, Osaka; Mitsubishi Denki Kabushiki Kaisha, Tokyo, both of Japan

[21] Appl. No.: 469,234

[22] Filed: Feb. 24, 1983

[30] Foreign Application Priority Data

Feb. 25, 1982 [JP] Japan .................................. 57-29685
Feb. 25, 1982 [JP] Japan .................................. 57-29686

[51] Int. Cl.⁴ .................................................. G01N 21/32
[52] U.S. Cl. ..................................... 356/237; 356/376
[58] Field of Search ............... 356/237, 376; 250/562, 250/563, 572, 223 R

[56] References Cited

U.S. PATENT DOCUMENTS 2,349,989 5/1944 Reason ................................ 356/376
3,816,746 6/1974 Gugliotta et al. .
4,315,688 2/1982 Pryor ............................ 356/237 X

FOREIGN PATENT DOCUMENTS

129585 12/1974 Japan .
111387 9/1976 Japan .
114261 9/1979 Japan .................................. 356/376
154402 12/1980 Japan .................................. 356/376
165705 10/1982 Japan .
414663 8/1934 United Kingdom ................ 356/237
1485449 9/1977 United Kingdom .

Primary Examiner—Davis L. Willis
Assistant Examiner—Matthew W. Koren
Attorney, Agent, or Firm—Burns, Doane, Swecker and Mathis

[57] ABSTRACT

A screw surface flaw inspection method and an apparatus therefor, which projects light onto the surface of a screw, the light being scanned axially of the screw, and a detector which picks up the reflected light from the projected surface and sends an output signal to a signal processing circuit to thereby detect the flaw on a basis of time base variation of the intensity of reflected light. The method and apparatus enables the inspection of minute flaws rapidly and exactly.

14 Claims, 21 Drawing Figures

SCREW SURFACE FLAW INSPECTION METHOD AND AN APPARATUS THEREFOR

FIELD OF THE INVENTION

This invention relates to an optical inspection method for the surface flaw at screw thread during the machining process of the screw and to an apparatus for practical use of the inspection method.

BACKGROUND OF THE INVENTION

It is indispensable for quality control to measure the screw thread elements, such as pitch, lead and height, and inspect the surface flaw of screw thread. The measurement has hitheto been performed by use of contact instruments, such as various gauges, and various attempts have been made for automatization of measurement, but the inspection of surface flaw depends almost on visual inspection not to have till now realized a practical automatic inspection method and apparatus. Accordingly, the present invention is intended to propose a method and an apparatus for automatically inspecting the surface flaw at the screw.

Figure 1:
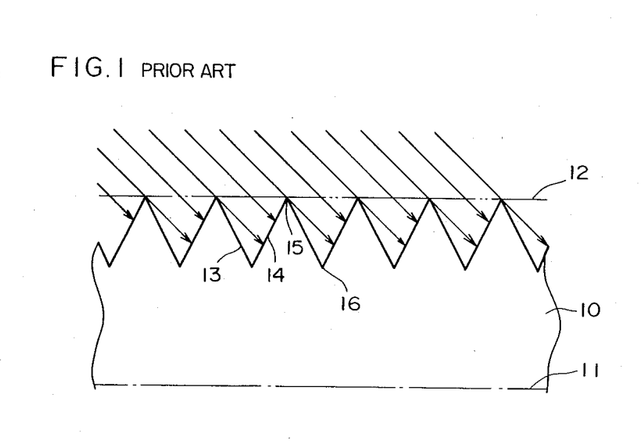
FIG. 1 is an illustration of the inspection principle of the prior art.
Figure 2:
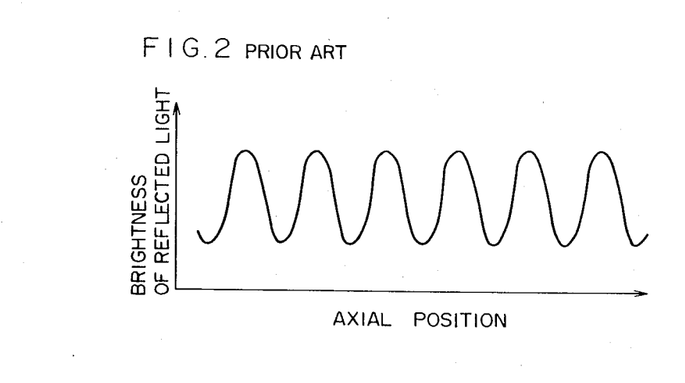
FIG. 2 shows a brightness of reflected light pattern corresponding to FIG. 1.
Figure 3:
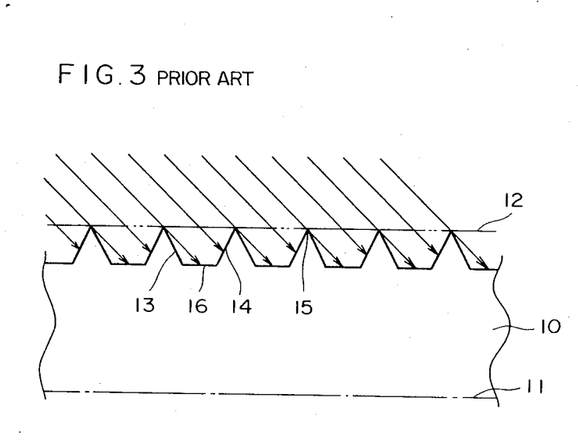
FIG. 3 is an illustration of the prior art when the flaw exists on the surface of screw.
Figure 4:
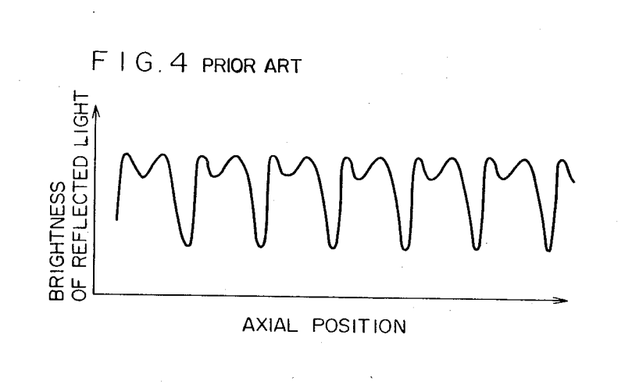
FIG. 4 shows a brightness of reflected light corresponding to FIG. 3.

The prior art of such inspection apparatus has been disclosed in the Japanese Patent Kokai No. 54-150163. Next, explanation will be given on the above in accordance with FIG. 1. A screw 10, as shown in FIG. 1, is irradiated with the light in the oblique direction with respect to the screw 10 and not-perpendicular with respect to the axis 11 thereof or the enveloping surface 12, so that one flank 13 is overall shaded and the other flank 14 is in part shaded, whereby when an image of screw 10 is picked up perpendicularly to the axis 11 or enveloping surface 12, optical information is obtainable which shows the distribution of the reflected light whose brightness at the shaded portion has a low level. Also, in a case where no flaw exists on the surface of screw thread, the optical information shows a regular bright-dark alternating pattern as shown in FIG. 2. On the contrary, for example, in a case where the flaw at the not-machined root exists as shown in FIG. 3, the light receiving flank 14 is irradiated overall to the root side, but the reflection brightness toward an image pickup apparatus is low at the corner between the flank 14 and the flat root 16, so that the brightness of the reflected light distribution is as shown in FIG. 4, in which the regular bright and dark pattern as in FIG. 2 is not obtained, but an irregular bright and dark pattern is obtained as shown in FIG. 4. Although such pattern makes it possible to detect various surface flaw, the inspection apparatus of the prior art, as understood from the aforesaid measurement principle, can detect large flaw in the thread elements, such as improper height and pitch. Hence, it has been absolutely impossible to inspect a minute surface flaw at the screw thread, such inspection having conventionally inevitably relied on the visual inspection and being the object for inspection by the present invention.

OBJECTS OF THE INVENTION

An object of the invention is to provide an optical inspection method and an apparatus therefor, capable of automatically detecting at high speed and with accuracy minute surface flaws called the nick or gouge, tool mark or the like at a screw.

Another object of the invention is to provide an inspection method and an apparatus therefor, capable of any minute flaw at the overall surface, i.e., throughout the crest, root and flank, of the screw thread.

Still another object of the invention is to provide a screw surface flaw inspection method and an apparatus therefor, which need only be provided with a photoelectric transducer to pick up the reflected light from the screw surface, thereby simplifying a signal processing circuit for a signal obtained by the photoelectric transducer.

A further object of the invention is to provide a screw surface flaw inspection method and an apparatus therefor, capable of locating the position of flaw on the crest, root or flank.

A still further object of the invention is to provide an inspection apparatus which is capable of detecting abnormality in a signal caused by the flaw from an output of the photoelectric transducer regardless of variations of flaws to thereby enable the exact flaw inspection, and which has a circuit simple in construction.

Yet another object of the invention is to provide a screw thread surface flaw inspection apparatus capable of automatically inspecting the overall peripheral surface of the screw.

These and other objects of the invention will become more apparent in the detailed description and examples which follow.

DETAILED DESCRIPTION OF THE INVENTION

The screw surface flaw inspection method is characterized basically in that the light spot is projected on the surface of a screw and scanned axially of the screw to pick up the reflected light from the projected surface, thereby detecting the screw surface flaw on a basis of information of a time base variation of the intensity of reflected light.

Figure 5:
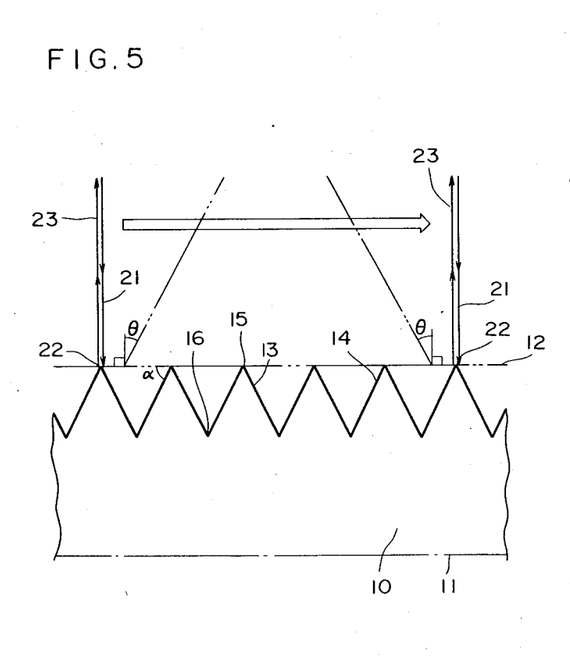
FIG. 5 is a view explanatory of the principle of an embodiment of an inspection method of the invention.

Firstly, explanation will be given on the principle of the invention. The profile of a screw 10 is shown in FIG. 5, in which the light beam directing toward the axis 11 of screw 10 and perpendicular to the axis 11 or the enveloping surface 12 of screw 10 is projected onto the surface of screw 10 to thereby form the light spot 22 on the surface thereof. Then, the light beam is moved, for example, in parallel to the axis 11 to perform scanning by the light spot 22. During the scanning, a photoelectric transducer picks up the reflected light 23 from the screw surface to obtain a photoelectric conversion signal. In addition, the photoelectric transducer may move together with the scan of light spot 22, or may have a length enough to receive the reflected light from within the scanning range.

Figure 6:
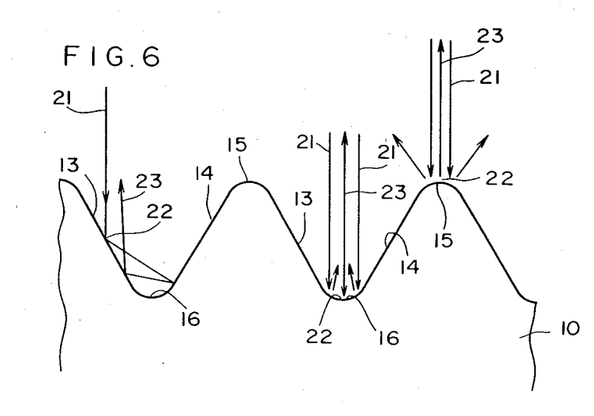
FIG. 6 is a view exemplary of the light spots in reflection condition.

FIG. 6 is an enlarged view exemplary of the profile of screw 10, in which the light spot 22 projected onto the crest 15 or the screw thread is reflected at the crest portion in the direction of projecting the light beam 21 because the crest 15 acts as the convex mirror, but the reflection of the light spot 22 is diffused as it approaches a flank 13 or 14. On the other hand, the light spot 22 projected on the root 16 of the screw thread is reflected from the root 16 in the direction of projecting the light beam 21 due to the function of root 16 like the concave mirror, but the reflection of the light spot 22 in the vicinity of flank 13 or 14 is converged and then diffused outside the screw 10. The lights reflected from the flanks 13 and 14 are under the multiple reflection therebetween to be widely diffused. Hence, the time base variation in the level of intensity of reflected light picked up by the photoelectric transducer, or of an electric signal output from the transducer, becomes the maximum value during the projecting of the light spots 22 on the crest 15 and root 16 of screw 10 and has a low level when on the flank 13 or 14 as shown in the waveform chart of FIG. 7.

Figure 7:
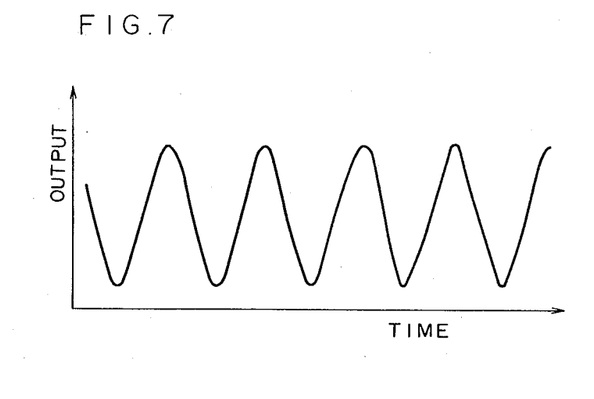
FIG. 7 is a waveform chart of a photoelectric transduced signal of the reflected light.

Now, in a case of being normal on the surface of screw 10, the signal indicating the above variation and regularly alternating as shown in FIG. 7 is obtained, but otherwise any flaws exist on the screw surface, the reflection mode of the flaw differs from the normal portion so that the signal is different in the repeating pattern from the above.

The inspection method of the invention is directed to inspection of the existence of flaw by detecting such abnormality of the signal. Next, the pattern of an output signal of the photoelectric transducer regarding the typical flaw of a screw member for coupling formed at the ends of an oil well pipe is shown.

Figure 8:
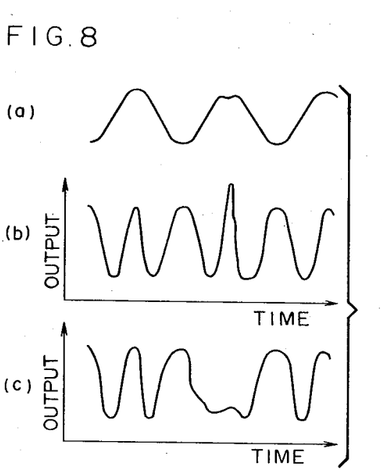
FIGS. 8 through 13 are waveform charts of photoelectric conversion signals corresponding to configurations of flaws respectively.

FIG. 8-(a) is a waveform showing the surface flaw called a nick or gouge, which is caused by a hit on a foreign object during the transport or handling and looks like a local dent or flatness on the surface of crest of screw thread. The waveform of signal for such flaw shows an extreme increase in the peak value corresponding to the crest of flaw as shown in FIG. 8-(b), or an extremely lowered reflection intensity from the crest as shown in FIG. 8-(c).

Figure 9:
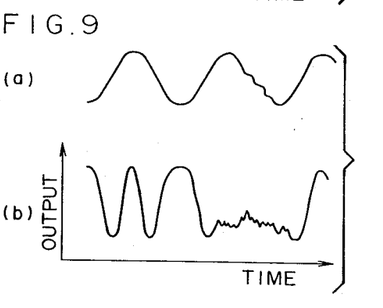

FIG. 9-(a) shows the flaw called a tool mark, which is caused by a poor tool or abnormal vibrations during the cutting of the screw and shows a slight roughness extending on the surface of the screw longitudinally or circumferentially thereof. Such flaw, as shown in FIG. 9-(b), lowers the intensity at the portion corresponding to the same so that sharp vibration of the low level is shown at the portions corresponding to the crest and flank.

Figure 10:
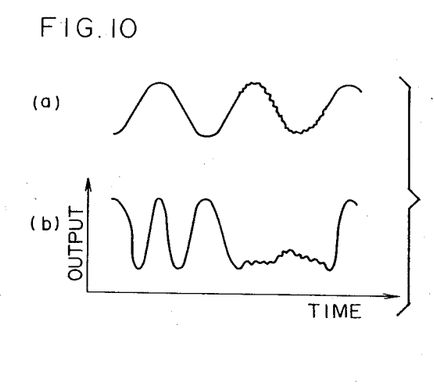

FIG. 10-(a) shows the flaw called a rough surface, which is caused by an improper combination of depth of cut and cutting speed of a cutter at a thread cutting device, or by entering of chips between the cutter and the screw. The surface of screw thread is scratched circumferentially to become irregularly rough so that the wave form of signal, as shown in FIG. 10-(b), lowers in the portion corresponding to the crest and shows gentle vibrations at the portions corresponding to the crest and flank.

Figure 11:
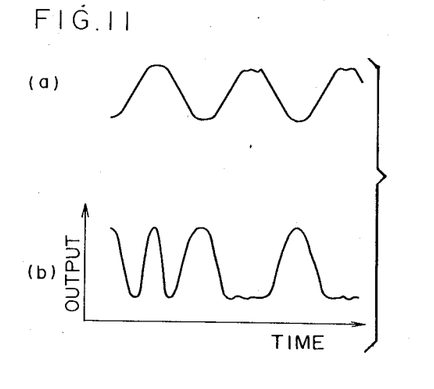

FIG. 11-(a) shows the surface flaw called the rust, which is the remainder of iron oxide on the surface not-cut away during the thread cutting, so that the rust portion becomes almost black not to reflect the light, while other portions are polished like the mirror, whereby the flat signal at the lower level is shown corresponding to the rust.

Figure 12:
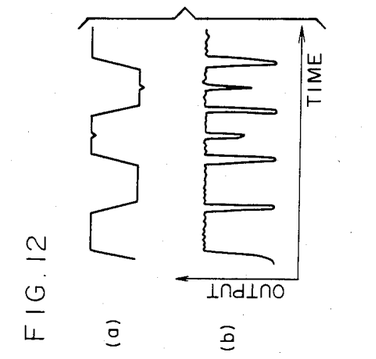

FIG. 12-(a) shows the surface flaw called a seam found in a trapezoidal screw thread, which is caused by folding, scratch or vacancy, of materials during the cutting, or by a minute break in a cutting tool and is found as the seam continuing circumferentially or axially at the top of flat crest or the bottom of root. Therefore, the signal, as shown in FIG. 12-(b), includes the portion which drop down during the output is flat and high level corresponding to the crest or root.

Figure 13:
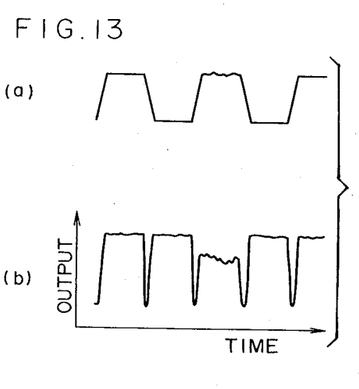

FIG. 13-(a) shows the surface flaw called a chip, which caused by contact with or a hit on a chuck at the thread cutting machine, so that in the trapezoidal screw thread, the flat portion at the crest is locally broken to be rough and not reflective. Hence, the signal, as shown in FIG. 13-(b), shows a low level only at the chip portion.

The abnormal signal components as abovementioned are ensured of detection by a signal processing circuit to be discussed below.

Next, explanation will be given on the projecting direction of the light beam 21 for forming the light spot 22. Firstly, as to the axial direction, in the embodiment shown in FIG. 5, a projection angle (which is defined as the angle between the light beam and the normal to the axis 11 or employing surface 12) of the light beam or light spot with respect to the axis 11 or enveloping surface 12 in the FIG. 5 embodiment is a zero degree, but the zero projection angle need not be made through out length of the scanning region. In other words, the projecting angle $\theta$ with respect to the axis 11 or enveloping surface 12, as shown in the alternate long and two short dashes line, is assumed to be included in a range of an angle smaller than the complementary angle $(90° - \alpha)$ to an angle $\alpha$ between the enveloping surface 12 and the flank 13 or 14. Under this condition, there is no shade caused by the crest 15 or screw thread so that the light spot 22 can be projected overall the crest 15, root 16 and flanks 13 and 14 to thereby enable inspection throughout the area. Also, the light spot 22 can scan not only by parallel movement but by swinging motion of the light source, thereby increasing the flexibility in construction of optical system.

Figure 14:
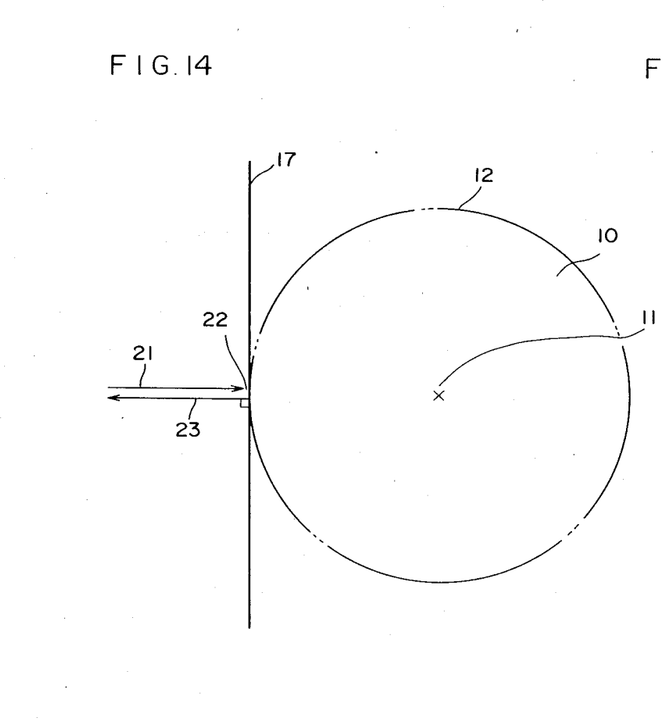
FIGS. 14 and 15 are views explanatory of the light spot projection direction shown together with the cross section of screw thread.

On the other hand, as to the radial direction, in the FIG. 5 embodiment, the light beam 21 is adapted to be directed toward the axis of screw 10. Referring to FIG. 14, the mode of projection and reflection of light spot is shown together with a cross-section of screw, in which the projection angle with respect to the tangent to the screw surface is made 0° (the projection angle is defined as aforesaid to be an angle between the light beam and the normal to the screw surface). In such case of performing the projection and reflection, the reflected light 23, which travels radially, will travel in the projecting direction. Therefore, the aforesaid projection angle need not be strictly zero, and an angle within a range corresponding to a diameter of light spot and a light-receiving area of photoelectric transducer, is allowed, the projection angle being enough to pick up the reflected light of the light spot by use of one photoelectric transducer.

Figure 15:
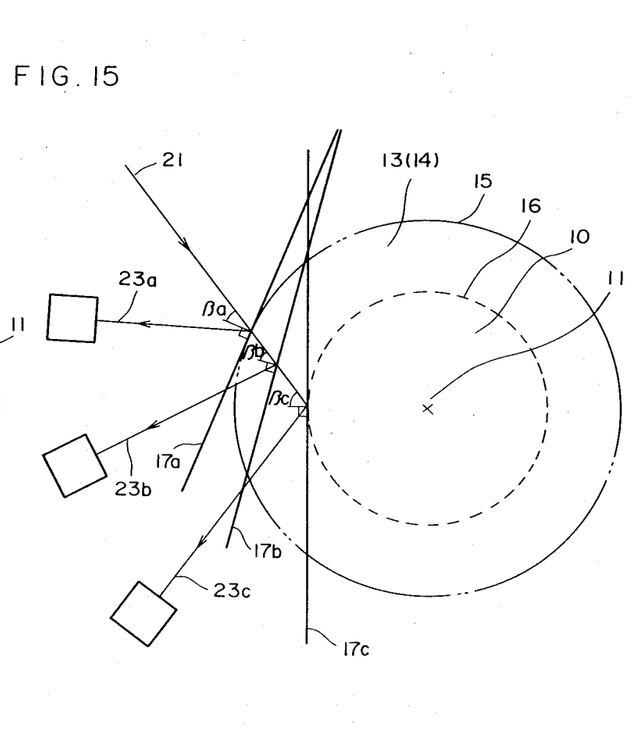

FIG. 15 shows another projecting method in which the projection angle with respect to the tangent 17 to the screw surface is not 0°. Thus, in a case of performing the projection of light beam, the projection angles with respect to the tangents 17a, 17b and 17c, when the light spot 22 is positioned at the crest 15, flanks 13 and 14, and root 16, are differenct as $\beta a$, $\beta b$ and $\beta c$, thereby leading to different directions of reflected lights 23a, 23b, or 23c. Accordingly, in such case of projecting the light beam, the photoelectric transducers are provided at the circumferentially different positions so as to separately receive the reflected light 23a, 23b or 23c so that the output of each photoelectric transducer is used as the signal for inspecting the surface flaw. In brief, the location of flaw can be discriminated independently of the crest 15, flanks 13, 14 or root 16. In addition, as to the projecting angle, the photoelectric transducer for receiving the reflected light 23b from the flank can of course be used also as that for the crest 15 or root 16.

Figure 16:
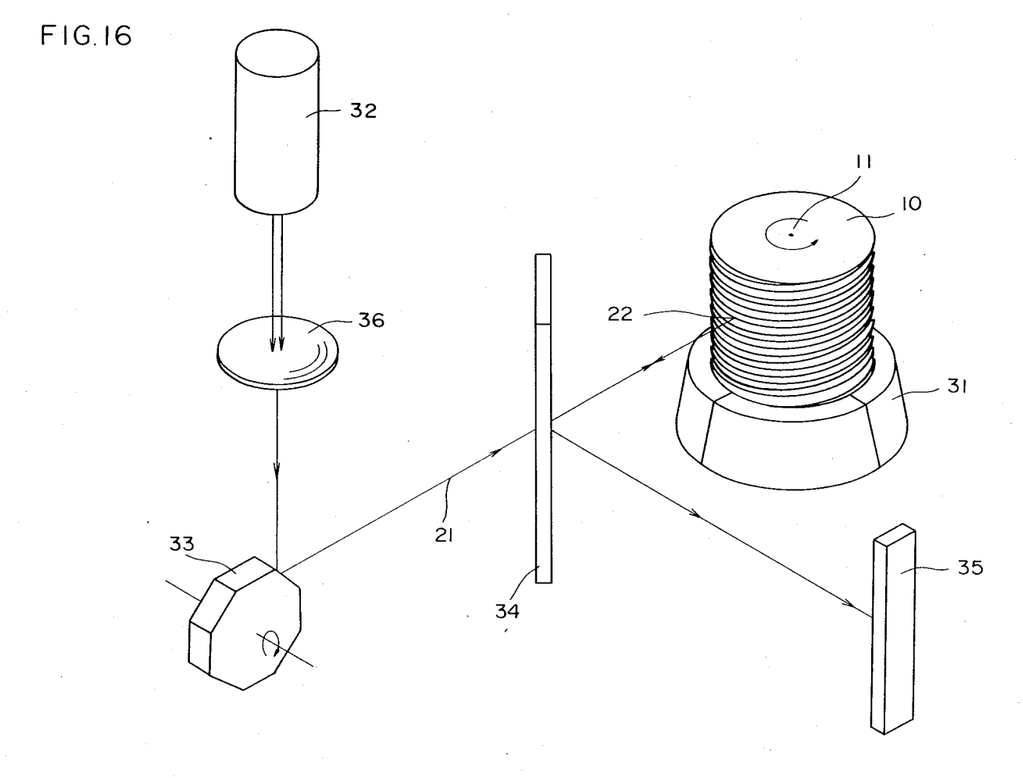
FIGS. 16 and 17 are views exemplary of construction of the optical system of an embodiment of an apparatus of the invention.

Next, explanation will be given on an apparatus for practical use of the inspection method of the invention. FIG. 16 is a schematic view explanatory of the optical system of the apparatus, in which a screw 10 is supported perpendicularly to a rotary chuck 31 and rotatable around the axis 11.

A laser beam oscilator 32 is provided apart at a proper distance from the screw 10 and a laser beam 21 from the laser beam oscillator 32 is projected through a condenser lens 36 to a scanning rotary mirror 33 polygonal and having a rotary shaft kept horizontal, reflected from the mirror 33, and then projected to the surface of screw 10 to form the light spot 22, the laser beam oscillator 32 and rotary mirror 33 being disposed so that the light spot 22 scans axially of screw 10 by rotation of rotary mirror 33 at high speed. In addition, the light source is not limited to the laser beam oscillator but need only form the light spot of a proper diameter. Also, the scanning means for light spot 22 is not limited to the rotary mirror, but enough to allow the light spot 22 to scan in the predetermined length, for example, an galvanometric scanner or ultrasonic deflection being desirably applicable. The projecting angle of laser beam 21 on the screw 10 is different in the upper and lower portions thereof, but the rotary mirror 33 and screw 10 are defined to have a distance therebetween so as to meet the aforesaid condition. Also, in this embodiment, the laser beam oscillator 32, rotary mirror 33 and screw 10 are so arranged that the laser beam travels toward the axis 11 as the same as shown in FIG. 14.

A beam splitter 34 is interposed in the passage of laser beam 21 between the rotary mirror 33 and the screw 10, the beam splitter 34 being adapted to shift the optical path of reflected light 23 from that of projecting light so that the reflected light 23 travels toward a photoelectric transducer 35.

The photoelectric transducer 35 comprises an element about equal in vertical length to the scanning range of the light spot 22 and small in width and need only output a voltage signal of the level corresponding to the intensity of received light, for example, PIN PHOTODIODE PIN-L9 manufactured by the UNITED DETECTOR TECHNOLOGY being applicable. In addition, a desired filter need only be provided before the photoelectric transducer not to be affected by the light other than the laser beam.

In the aforesaid apparatus, the laser beam oscillator 32 is kept in oscillation condition, the rotary mirror 33 rotates at high speed, and the rotary chuck 31 rotates at the predetermined speed, thereby applying to the light spot 22 the main scanning axial of screw 10 and the subscanning circumferential thereof, the photoelectric transducer 35 picking up the reflected light from the scanning range.

In addition, the photoelectric transducer can be reduced in vertical length by interposing a condenser lens or an optical fiber bundle between the beam splitter 34 and the photoelectric transducer 35. Also, in a case where the light spot scanning range to meet the condition of projection angle about axial direction of screw 10 is of smaller length than a full axial length of the screw, a rotary chuck provided with lifting function is used to perform the inspection in condition of satisfying the aforesaid condition. The scanning means for light spot about circumferential direction of the screw is not limited to the abovementioned construction, but the scanning means for revolving the light source around the screw is applicable.

Figure 17:
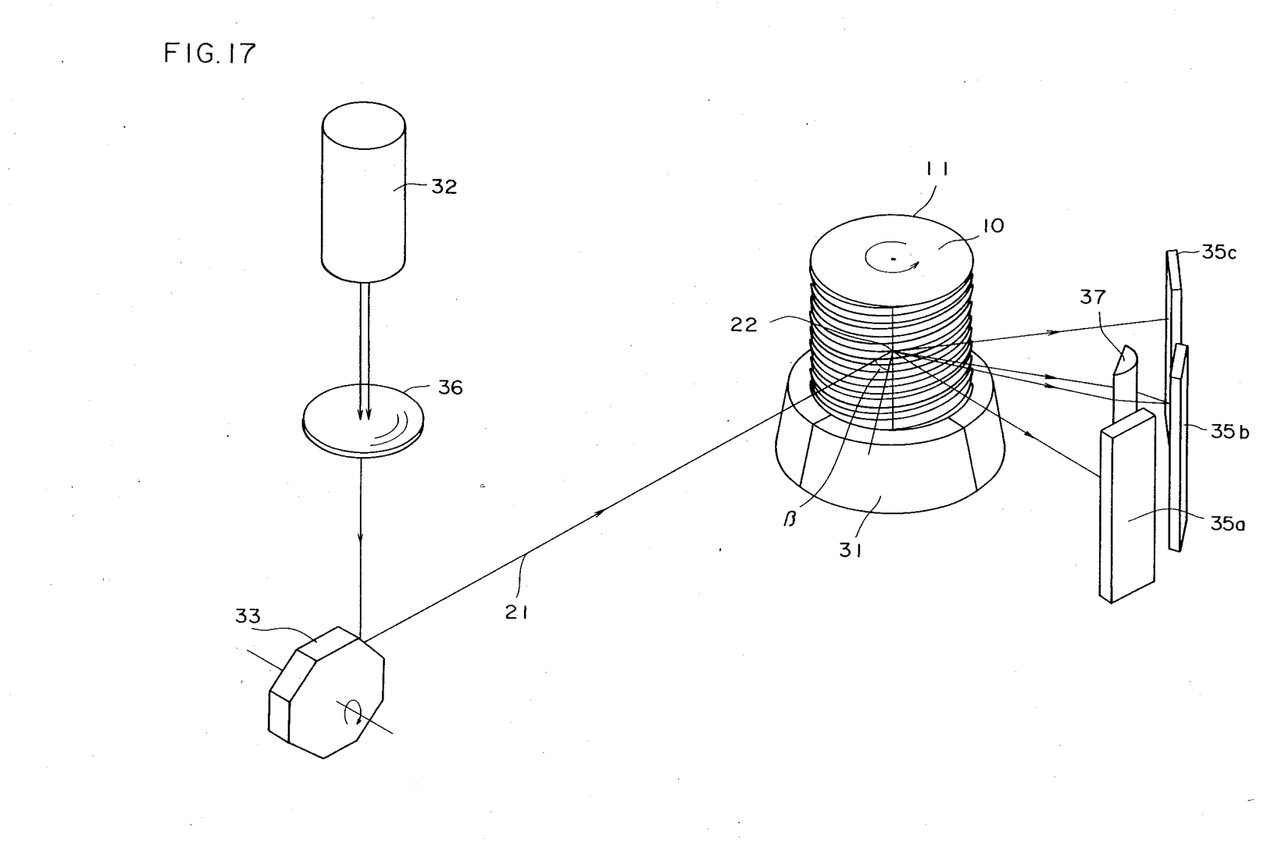

FIG. 17 is a schematic view of the optical system at the apparatus of the invention when applied with the method of not making the projection angle zero as shown in FIG. 15, in which the screw 10 is supported vertically to a rotary chuck 31 so as to be rotatable around the axis 11.

A laser beam oscillator 32 is provided apart at a proper distance from the screw 10, so that the laser beam 21 oscillated from the laser beam oscillator 32 is projected through a condenser lens 36 to a polygonal scanning rotary mirror 33 keeping its rotary shaft horizontal, and is reflected from the mirror 33 to be projected onto the surface of screw 10 in relation of making the projection angle about radial direction of screw not zero but $\beta$, thereby forming the light spot 22, the laser beam oscillator 32 and rotary mirror 33 being arranged to allow the light spot 22 to scan axially of screw 10 by means of rotation of rotary mirror 33 at high speed. In addition, the projection angle of laser beam 21 with respect to the axial direction of screw 10 is conditioned as the same as the embodiment shown in FIG. 16.

The reflection angles of the light from the crest 15, flanks 13 and 14, and root 16, are different from each other, so that three photoelectric transducers 35a, 35b and 35c are juxtaposed to enable reception of each reflected light, the photoelectric transducers 35a, 35b and 35c, being the same as the aforesaid photoelectric transducer 35. The diffusion of reflected light from the flanks 13 and 14 for the direction of the axial direction of screw 10, as abovementioned, is utilized by itself to discriminate from the crest 15, the root 16, but the circumferential or radial diffusion leads merely to scattering of the flaw information, whereby a condenser lens 37 is to be disposed in front of photoelectric transducer 35b for focusing the light efficiently thereon.

Next, explanation will be given on a circuit for processing an output signal of photoelectric transducer and indicating the existence of flaw, which circuit is exemplified in FIG. 18. For example, an output signal [FIG. 19-(1)] of photoelectric transducer 35a is given to digitizers 40 and 41, into which threshold values $V_1$ and $V_2$ ($V_2 > V_1$) are set respectively. The digitizers 40 and 41 compare input signals with the values $V_1$ and $V_2$, and, when the input signals are higher in level than $V_1$ and $V_2$, output signals of high level respectively, the threshold value $V_1$, as shown in FIG. 19-(1), being selected to be slightly lower than the maximum value in the repetition pattern and that $V_2$, as shown in FIG. 19-(1), slightly higher than said maximum value.

Figure 19:
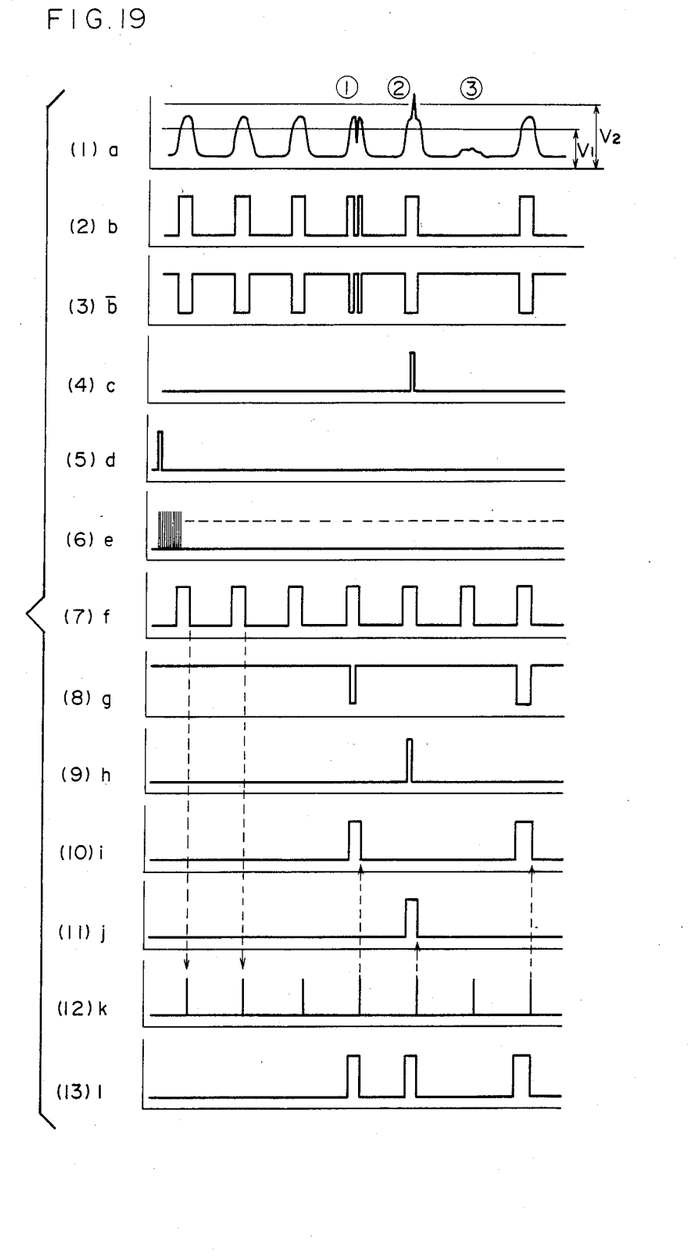
FIG. 19 is a time chart explanatory of operation of the apparatus shown in FIG. 18.

Now, when we assume the flaw exists on the top of crest, a variation occurs in the signal as shown in FIGS. 8 through 13, which is classified as follows:

a change, as shown in ① in FIG. 19-(1), to instantaneously fall at the portion of the peak value down to a lower level than $V_1$, that, as shown in ② in FIG. 19-(1), to instantaneously rise at the peak up to a higher level than $V_2$, and that, as shown in ③ in FIG. 19-(1), to fall at the peak to a lower level than $V_1$. The output signals b and c of digitizers 40 and 41, when such changes of ①, ② and ③ are input, are shown by FIGS. 19-(2) and -(4), the output signal b being inverted by an inverter 44 so that the inverted signal $\overline{b}$ FIG. 19-(3) is given to a NAND gate 45, the output signal c given to a NAND gate 46.

Figure 18:
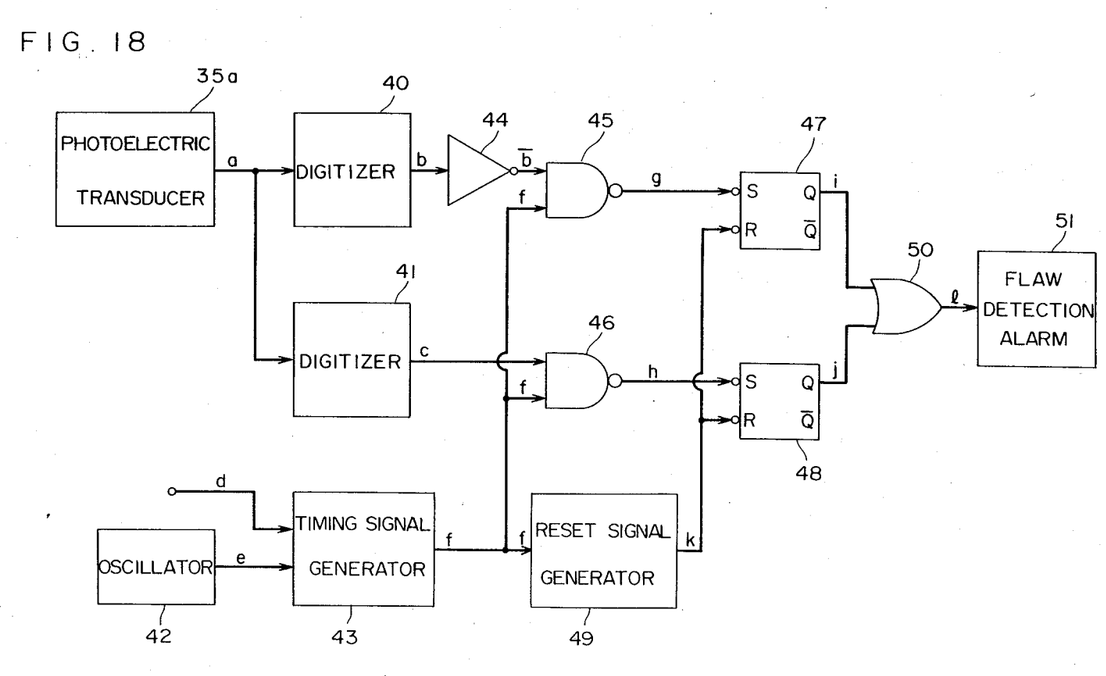
FIG. 18 is a circuit diagram of a signal processing circuit of the apparatus of the invention.

In FIG. 18, reference numeral 43 designates a timing signal generator, which is given a synchronizing signal d [FIG. 19-(5)] in synchronism with the start of scanning for the light spot 22 and a clock signal e [FIG. 19-(6)] generated by an oscillator 42, thereby frequency-dividing and outputting on a basis of the signals d and e a timing signal f [FIG. 19-(7)] of a high level for a proper time before and after the peak of signal a inclusive thereof, in other words, at the time period when the crest portion of screw thread is scanned, the timing signal f being given to another inputs of NAND gates 45 and 46 respectively and also given to a reset signal generator 49. The reset signal generator 49 outputs an instantaneous pulse as a reset pulse k at the trailing edge of timing signal f given to the reset signal generator 49, as shown in FIG. 19-(12), the reset pulse k being given to the reset terminals of R-S flip-flops 47 and 48 respectively. The output signals g and h are given to the set terminals of R-S flip-flops 47 and 48 respectively, the set terminals being active by the input of low level to set the R-S flip-flops 47 and 48 respectively. The set outputs i and j [FIGS. 19-(10) and (11)] of R-S flip-flops 47 and 48 are fed to an OR gate 50, so that an output l [(FIG. 19-(13)] thereof, when having a high level, is adapted to actuate a flaw detection alarm 51.

In a case of occurrence of the signal variation corresponding to the flaw as shown by ①, the output b of digitizer 40 proceeds in the regular repetition of high and low levels and instantaneously falls to a low level during the high level, whereby the output g of NAND gate 45 instantaneously falls to a low level to set the R-S flip-flop 47, the set output i thereof having a high level until it is reset by the reset pulse k, and the output l of OR gate 50 also having a high level, thus detecting the existence of flaw.

In a case of occurrence of the signal variation corresponding to the flaw as shown by ②, the output c of digitizer 41 instantaneously has a high level, thereby setting the R-S flip-flop 48. The set output j thereof keeps a high level until it is reset by the reset pulse k, whereby the output l of OR gate 50 also has a high level to thereby detect the existence of flaw.

In a case of occurrence of the signal variation corresponding to the flaw as shown by ③, the output b of digitizer 40 or the output $\overline{b}$ of inverter 44, is in condition of showing lack of pulse, so that both the inputs to the NAND gate 45 have high levels at the timing of lack of pulse to thereby set the flip-flop 47. As a result, the output l of OR gate 50 has a high level to detect the existence of flaw.

As seen from the above, the NAND gates 45 and 46 are open only when the timing signal f is generated, so that noises, even when picked up with the timing for scanning of light spot on other portions (the portions other than the crest in this embodiment), can be eliminated to thereby avoid a false detection indication.

Also, since the R-S flip-flops 47 and 48 are set at the low level by the inputs of low level given to the set terminals and kept in this condition for a while, the flaw even minute can be detected and indicated with accuracy. In addition, the signal regarding the reflected light from the flank or root can be processed quite in the same manner.

The above signal processing circuit is so constructed that the digitizer detects that nonrepetition of the same patterns about photoelectric transducer. Next, explanation will be given on a circuit which stores the signal repetition pattern itself and reads out it repeatedly and compares the read-out content with the outputs of photoelectric transducer sequentially given to the circuit to thereby be intended to detect the existence of the flaw.

Figure 20:
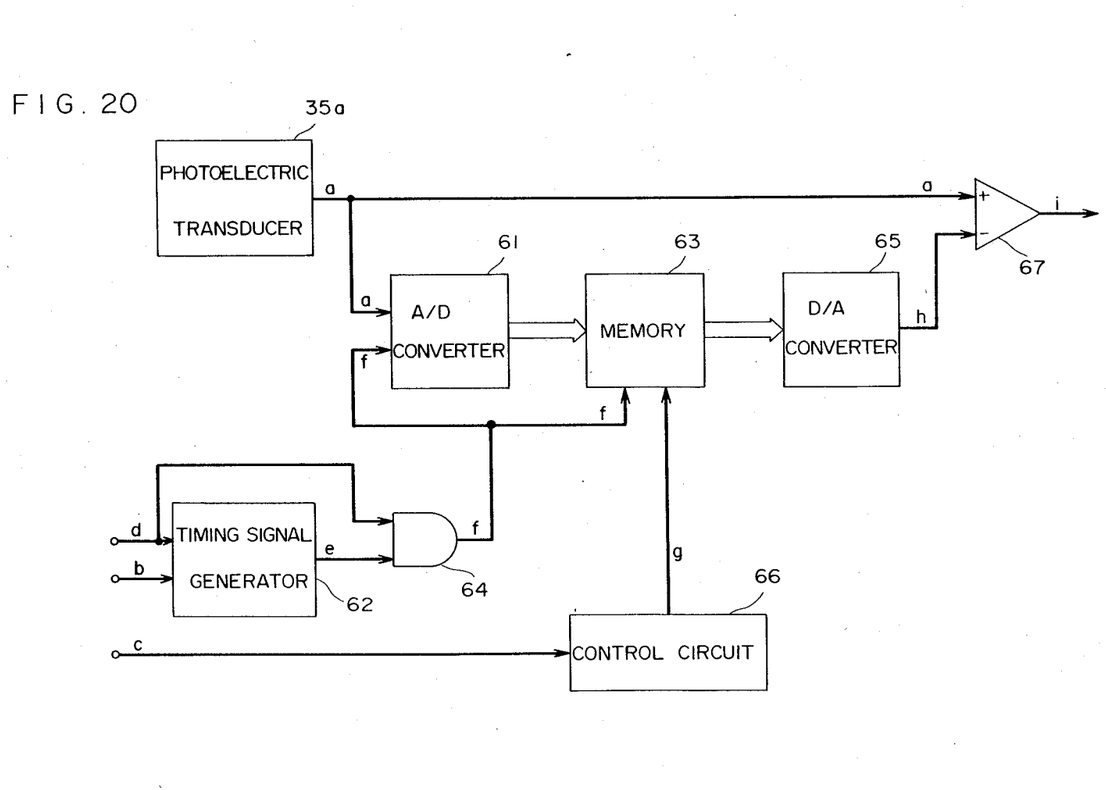
FIG. 20 is a circuit diagram of a signal processing circuit of a modified embodiment of the apparatus of the invention.
Figure 21:
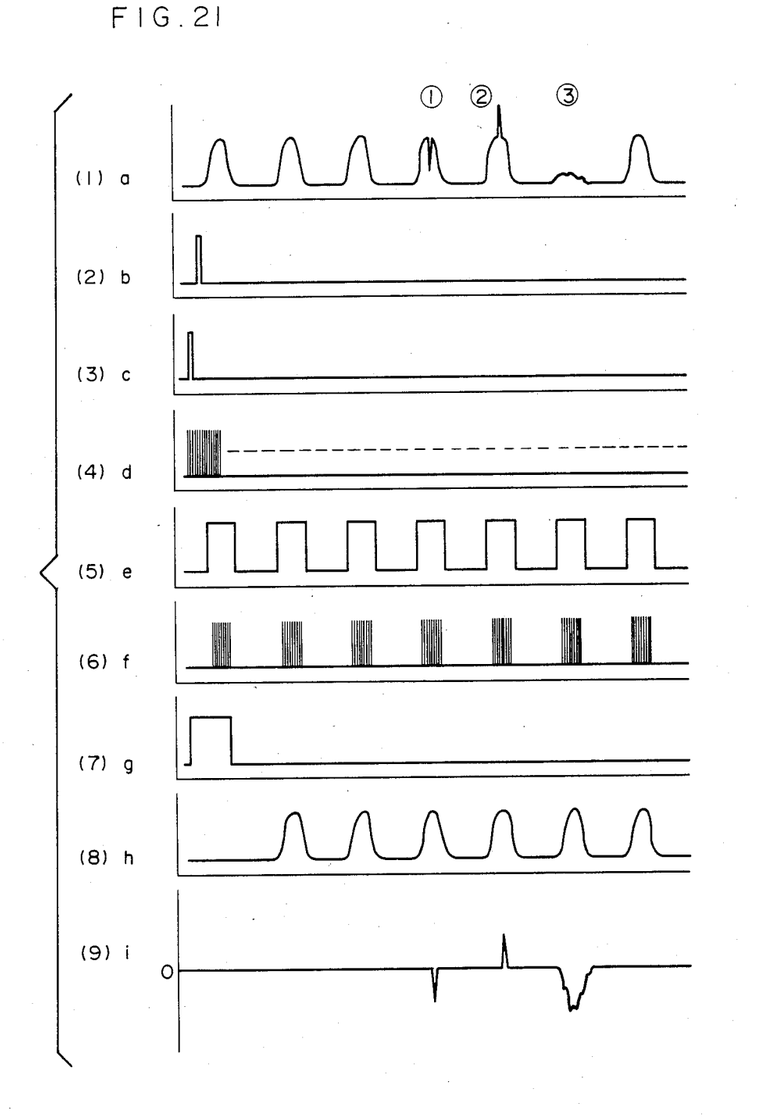
FIG. 21 is a time chart explanatory of operation of the embodiment shown in FIG. 20.

FIG. 20 shows a circuit diagram of the above signal processing circuit. For example, an output signal a [FIG. 21-(1)] of photoelectric transducer 35a is given to the plus input terminal of a differential amplifier 67 and also to an A/D (analog-to-digital) converter 61. A timing signal generator 62 is the same as the timing generator 43 in FIG. 18, is given a high frequency clock signal d [FIG. 21-(4)] necessary for sampling the output signal a of photoelectric trnasducer 35a and a synchronizing signal b [FIG. 21-(2)] given in synchronism with the start of scanning of the light spot 22, and demultiply-outputs in frequency division a timing signal e [FIG. 21-(5)] which has a high level for the proper time before and after the signal a inclusive of the peak thereof, in other words, at the time period of scanning the crest portion of screw thread, the timing signal e being given to one input terminal of an AND gate 64, the clock signal d to another input terminal of the same. Hence, the output of AND gate 64 is represented by a signal f [FIG. 21-(6)] of intermittently appearing clock signal. A control circuit 66 for a memory 63 receives a system start signal c given prior to the synchronizing signal b and keeps its output signal g [FIG. 21-(7)] in a high level for the predetermined time, the output signal g being given to the memory 63 as the write/read control signal and performing write-in for the high level and read-out for the low level. In addition, the time period of keeping the outut signal g at a high level has been set somewhat larger than a pulse width of signal e.

The signal f is given to the A/D converter 61 as the clock signal for sampling and to the memory 63 as the increment signal for its address counter. The memory 63 functions in a write mode during the high level of output signal g of control circuit 66 so that the discrete data of the waveform of signal a, applied by the signal f with sampling of the content, as the write-in address, of address counter incremented by the signal f is sequentially written-in. On the other hand, after the signal g has a low level, the memory 63 functions in a read-out mode so that the contents of address counter incremented by the signal f is used as the read address to read the stored content of memory 63. The data read out from the memory 63 is given to a D/A (digital-to-analog) converter 64 and converted therein to the analogue signal. Hence, the output of D/A converter 65 becomes an analogue signal h [FIG. 21-(8)] repeatedly reproducing the waveform of signal a during the high level of signal g, the analogue signal h being given to the minus terminal of differential amplifier 67 so that a signal corresponding to a difference between both the inputs is amplified and output as the output signal i from the differential amplifier 67, the output signal i being given to a proper flaw detection and indication circuit.

Thus, in the signal processing circuit, both the inputs of differential amplifier are equal to each other when no signal change is caused by the flaw, whereby the output signal i is kept in the zero level. However, in a case of occurrence of the signal variation shown by ①, ② or ③, the output signal i will represent variation corresponding to the above, thereby enabling flaw detection with accuracy. Alternatively, the repetition pattern of signal a to be stored in memory 61 may include a plurality of cycles, but not be limited to one cycle and also data of one cycle obtained by average-processing data of plurality of cycles may be stored.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within meets and bounds of the claims, or equivalence of such meets and bounds thereof are therefore intended to be embraced by the claims.

What is claimed is:

1. A method of detecting flaws on a surface of a screw, comprising the steps of:
    projecting a light beam onto the surface of the screw at an angle to an enveloping surface of the screw that is smaller than a complementary angle between a flank of a screw thread and said enveloping surface in a manner to be reflected therefrom;
    moving the light beam along the surface of the screw to scan the surface of the screw;
    detecting the intensity of light reflected from said screw as the light beam moves therealong; and
    detecting a surface flaw of said screw based on a time base variation of the intensity of said reflected light.

2. A method as set forth in claim 1, wherein the step of projecting a light beam includes projecting the light beam at an angle with respect to a tangent to the surface of said screw and to a radial direction of said screw that is substantially zero.

3. A method as set forth in claim 1, wherein the step of projecting a light beam includes projecting the light beam at a predetermined angle with respect to a tangent to the surface of said screw and to a radial direction of said screw.

4. A method of detecting flaws on a surface of a screw, comprising the steps of:
    projecting a light beam onto the surface of the screw at a predetermined angle with respect to a tangent to the surface of said screw and to a radial direction of said screw in a manner to be relfected therefrom;
    moving the light beam along the surface of the screw to scan the surface of the screw;
    detecting the intensity of light reflected from said screw as the light beam moves therealong; and
    detecting a surface flaw of said screw based on a time base variation of the intensity of said reflected light.

5. A screw surface flaw inspection apparatus, comprising:
    means for projecting a light beam on a surface of a screw in a manner to be reflected therefrom;
    means for moving said light beam along said surface in an axial direction of said screw;
    at least one photoelectric transducer for converting said reflected light into a voltage signal; and
    a signal processing circuit for measuring said voltage signal and for detecting a variation of said signal when said signal varies from a predetermined repetition pattern, said signal processing circuit including:
    a plurality of digitizers having different threshold levels;
    a discriminator circuit for discriminating the outputs of said digitizers from noise in connection with scanned light; and
    a holding circuit for holding the outputof said discrimination circuit for a predetermined time.

6. A screw surface flaw inspection apparatus as set forth in claim 5, wherein said at least one photoelectric transducer is disposed to detect reflected light from a crest, root or flank of said screw.

7. A screw surface flaw inspection apparatus as set forth in claim 6, and further comprising means for changing the position of said light beam on said screw surface circumferentially of said screw.

8. A screw surface flaw inspection apparatus as set forth in claim 5, and further comprising means for changing the position of said light beam on said screw surface circumferentially of said screw.

9. A screw surface flaw inspection apparatus, comprising:
    means for projecting a light beam on a surface of a screw in a manner to be reflected therefrom;
    means for moving said light beam along said surface in an axial direction of said screw;
    at least one photoelectric transducer for converting said reflected light into a voltage signal; and
    a signal processing circuit for measuring said voltage signal and for detecting a variation of said signal when said signal varies from a predetermined repetition pattern, said signal processing circuit including:
    a memory for storing said signal for at least one cycle period in said repetition pattern;
    a read-out circuit for reading the contents of said memory; and
    means for comparing the contents of said memory read by said read-out circuit with the voltage signal from said photoelectric transducer.

10. A screw surface flaw inspection apparatus as set forth in claim 9, and further comprising means for changing the position of said light beam on said screw surface circumferentially of said screw.

11. A screw surface flaw inspection apparatus as set forth in claim 9, wherein said at least one photoelectric transducer is disposed to detect reflected light from a crest, root or flank of said screw.

12. A screw surface flaw inspection apparatus as set forth in claim 11, and further comprising means for changing the position of said light beam on said screw surface circumferentially of said screw.

13. A screw surface flaw inspection apparatus, comprising:
   means for projecting a light beam on a surface of a screw in a manner to be reflected therefrom;
   means for moving said light beam along said surface in an axial direction of said screw;
   at least one photoelectric transducer for converting said reflected light into a voltage signal;
   a signal processing circuit for measuring said voltage signal and for detecting a variation of said signal when said signal varies from a predetermined repetition pattern, and
   means for changing the position of said light beam on said screw surface circumferentially of said screw.

14. A screw surface flaw inspection apparatus as set forth in claim 13, wherein said at least one photoelectric transducer is disposed to detect reflected light from a crest, root or flank of said screw.

* * * * *